US012596110B2

(12) United States Patent
Lee et al.

(10) Patent No.: US 12,596,110 B2
(45) Date of Patent: Apr. 7, 2026

(54) SYSTEM FOR MEASURING ODOR AND METHOD FOR MEASURING ODOR USING THE SAME

(71) Applicants: Hyundai Motor Company, Seoul (KR); Kia Corporation, Seoul (KR)

(72) Inventors: Tae Hee Lee, Yongin-si (KR); Dae Un Sung, Incheon (KR)

(73) Assignees: Hyundai Motor Company, Seoul (KR); Kia Corporation, Seoul (KR)

( * ) Notice: Subject to any disclaimer, the term of this patent is extended or adjusted under 35 U.S.C. 154(b) by 422 days.

(21) Appl. No.: 18/464,488

(22) Filed: Sep. 11, 2023

(65) Prior Publication Data

US 2024/0369520 A1 Nov. 7, 2024

(30) Foreign Application Priority Data

May 3, 2023 (KR) ........................ 10-2023-0057422

(51) Int. Cl.
*G01N 33/00* (2006.01)
(52) U.S. Cl.
CPC ..... *G01N 33/0062* (2013.01); *G01N 33/0031* (2013.01); *G01N 33/0047* (2013.01); *G01N 33/0073* (2013.01)
(58) Field of Classification Search
CPC ........... G01N 33/0062; G01N 33/0009; G01N 33/0004; G01N 33/0073; G01N 33/0047
See application file for complete search history.

(56) References Cited

U.S. PATENT DOCUMENTS

2014/0345363 A1* 11/2014 Pretre ..................... G01N 7/00
73/25.03
2024/0142351 A1* 5/2024 Miller ................ G01N 33/0004

FOREIGN PATENT DOCUMENTS

JP 2005221464 A * 8/2005
KR 100794920 B1 1/2008
KR 20100004383 U 4/2010
WO 2017167671 A1 10/2017

OTHER PUBLICATIONS

Machine translation of JP 2005221464 (Year: 2005).*

* cited by examiner

*Primary Examiner* — Nathaniel J Kolb
(74) *Attorney, Agent, or Firm* — Slater Matsil, LLP

(57) ABSTRACT

In one embodiment, a system can be used for measuring odor data. The system includes an odor measurement chamber having a gas inlet and a gas outlet located at respective end portions of the odor measurement chamber. An inlet valve is mounted in the gas inlet and an outlet valve is mounted in the gas outlet. An odor sensor is disposed in the odor measurement chamber. A controller is configured to monitor first odor data of gas injected into the odor measurement chamber for a sensing time period of the odor sensor, to control the inlet valve and the outlet valve to close in response to a variation in the monitored first odor data being equal to or greater than a reference value, and then to acquire second odor data of the gas sensed by the odor sensor as actual odor data.

20 Claims, 6 Drawing Sheets

SYSTEM FOR MEASURING ODOR AND METHOD FOR MEASURING ODOR USING THE SAME

CROSS-REFERENCE TO RELATED APPLICATIONS

This application claims the benefit of Korean Patent Application No. 10-2023-0057422, filed on May 3, 2023, which application is hereby incorporated herein by reference.

TECHNICAL FIELD

The present disclosure relates to a system and method for measuring odor data.

BACKGROUND

As is well known, inherent odors and volatile organic compound (VOC) odors generated from various interior parts of vehicles, such as seat covers, head linings, door trims, and mats, are major causes of complaints about new vehicles.

In addition, an odor due to mold propagation caused by moisture condensed in an evaporator core during operation of an air conditioner of a vehicle also causes discomfort to vehicle users.

In addition, various kinds of odors may be included in external air flowing into vehicles during travel depending on the surrounding environment, and the odors introduced into vehicles from outside may also give vehicle users an unpleasant feeling.

The emotional quality of vehicles may be degraded due to various kinds of odors generated in the vehicles or introduced thereinto from outside.

Therefore, accurate odor sensing of an odor sensor and construction of odor data are required in order to analyze causes of various kinds of odors generated in vehicles or introduced thereinto from outside and to remove the odors. In addition, it is necessary to analyze the components of various kinds of odors generated in vehicles or introduced thereinto from outside and concentrations of the odor components in order to clearly identify actual causes of the odors.

In addition, in order to settle civil complaints related to odors generated in various industrial sites as well as in vehicles, it is necessary to accurately measure the components of odors and concentrations of the odor components by installing odor sensors in the corresponding industrial sites.

To this end, as conventional odor sensors for measuring odors generated in various industrial sites as well as in vehicles, electrochemical odor sensors and electrochemical odor sensor arrays may be used. Alternatively, odor biosensors, such as biopeptide-type sensors or sensors using amino acids, may be used. Odor sensors having various other structures are being developed.

However, electrochemical odor sensors have a limitation in being used as odor sensors for vehicles due to the low sensing accuracy, low durability, and very short lifespan thereof. Biopeptide-type sensors or sensors using amino acids are sensors that change in color in response to specific odor components and concentrations thereof and have an advantage of precise sensing response. However, biopeptide-type sensors or sensors using amino acids are very sensitive to ambient temperature and humidity, and thus, for example, have excessively high reactivity when humidity is high. Therefore, there is a limitation in accurately measuring odor data.

Furthermore, odor data that is measured by the conventional odor sensors may be acquired at predetermined measurement time intervals, or may be acquired as an average value of data acquired during a predetermined time period. However, the measurement accuracy of the conventional odor sensors may be low because odor components are not uniformly distributed in the air during a predetermined time period and the amount of odor components continuously changes over time.

The above information disclosed in this background section is only for enhancement of understanding of the background of embodiments of the invention, and therefore it may contain information that does not form the related art that is already known to a person of ordinary skill in the art.

SUMMARY

The present disclosure relates to a system and method for measuring odor data. Particular embodiments relate to an odor data measurement system and method capable of stably and accurately acquiring odor data obtained by odor sensing of an odor sensor in an odor measurement chamber.

Embodiments of the present invention can solve problems associated with the related art, and an embodiment of the present invention provides a system and method for measuring odor data, in which a gas, the odor of which is to be measured, is injected into an odor measurement chamber in which an odor sensor is disposed, odor data of the gas is monitored in real time by a controller during a sensing time period of the odor sensor, an inlet valve and an outlet valve mounted in the odor measurement chamber are controlled to close in order to confine the gas in the odor measurement chamber when variation in the monitored odor data is equal to or greater than a reference value, and thereafter odor data of the gas sensed by the odor sensor is acquired as actual odor data, whereby odor data may be obtained stably and accurately at all times.

An embodiment of the present invention provides a system for measuring odor data, the system including an odor measurement chamber including a gas inlet and a gas outlet formed in respective end portions thereof, an inlet valve mounted in the gas inlet so as to open and close, an outlet valve mounted in the gas outlet so as to open and close, an odor sensor disposed in the odor measurement chamber to sense an odor of a gas injected into the odor measurement chamber, and a controller configured to monitor first odor data of the gas for a sensing time period of the odor sensor, to control the inlet valve and the outlet valve to close when variation in the monitored first odor data is equal to or greater than a reference value, and then to acquire second odor data of the gas sensed by the odor sensor as actual odor data.

In a preferred embodiment, the controller may be configured to compare an odor pattern of the second odor data with a previously stored odor pattern, to perform display control indicating that the odor pattern of the second odor data is identical to the previously stored odor pattern upon determining that the odor pattern of the second odor data is identical to the previously stored odor pattern, and to store the odor pattern of the second odor data as a new odor pattern upon determining that the odor pattern of the second odor data is different from the previously stored odor pattern.

In another preferred embodiment, the controller may be configured to control the inlet valve and the outlet valve to open in order to measure an odor of a new gas after acquiring the second odor data.

Another embodiment of the present invention provides a method of measuring odor data, the method including injecting a gas, an odor of which is to be measured, into an odor measurement chamber, monitoring, by a controller, first odor data of the gas for a sensing time period of an odor sensor disposed in the odor measurement chamber when the odor sensor senses an odor of the gas, controlling, by the controller, an inlet valve and an outlet valve mounted in an inlet and an outlet of the odor measurement chamber, respectively, to close when variation in the monitored first odor data is equal to or greater than a reference value, and acquiring, by the controller, second odor data of the gas, sensed by the odor sensor in a state of confining the gas in the odor measurement chamber by closing the inlet valve and the outlet valve, as actual odor data.

In a preferred embodiment, the method may further include comparing, by the controller, an odor pattern of the second odor data with a previously stored odor pattern, performing, by the controller, display control indicating that the odor pattern of the second odor data is identical to the previously stored odor pattern upon determining that the odor pattern of the second odor data is identical to the previously stored odor pattern, and storing, by the controller, the odor pattern of the second odor data as a new odor pattern upon determining that the odor pattern of the second odor data is different from the previously stored odor pattern.

In another preferred embodiment, the method may further include controlling, by the controller, the inlet valve and the outlet valve to open in order to measure an odor of a new gas after acquiring the second odor data.

Another embodiment of the present invention provides a system for measuring odor data, the system including an odor measurement chamber including a gas inlet and a gas outlet formed in respective end portions thereof, an inlet valve mounted in the gas inlet so as to open and close, an outlet valve mounted in the gas outlet so as to open and close, a first odor sensor and a second odor sensor disposed in the odor measurement chamber to sense an odor of a gas injected into the odor measurement chamber, and a controller configured to monitor first odor data of the gas for a sensing time period of the first odor sensor, to control the inlet valve and the outlet valve to close when variation in the monitored first odor data is equal to or greater than a reference value, and then to acquire second odor data of the gas sensed by the second odor sensor as actual odor data.

In a preferred embodiment, the controller may be configured to compare an odor pattern of the second odor data with a previously stored odor pattern, to perform display control indicating that the odor pattern of the second odor data is identical to the previously stored odor pattern upon determining that the odor pattern of the second odor data is identical to the previously stored odor pattern, and to store the odor pattern of the second odor data as a new odor pattern upon determining that the odor pattern of the second odor data is different from the previously stored odor pattern.

In another preferred embodiment, the controller may be configured to control the inlet valve and the outlet valve to open in order to measure an odor of a new gas after acquiring the second odor data.

Another embodiment of the present invention provides a method of measuring odor data, the method including injecting a gas, an odor of which is to be measured, into an odor measurement chamber, monitoring, by a controller, first odor data of the gas for a sensing time period of a first odor sensor disposed in the odor measurement chamber when the first odor sensor senses an odor of the gas, controlling, by the controller, an inlet valve and an outlet valve mounted in an inlet and an outlet of the odor measurement chamber, respectively, to close when variation in the monitored first odor data is equal to or greater than a reference value, and acquiring, by the controller, second odor data of the gas, sensed by a second odor sensor disposed in the odor measurement chamber in a state of confining the gas in the odor measurement chamber by closing the inlet valve and the outlet valve, as actual odor data.

In a preferred embodiment, the method may further include comparing, by the controller, an odor pattern of the second odor data with a previously stored odor pattern, performing, by the controller, display control indicating that the odor pattern of the second odor data is identical to the previously stored odor pattern upon determining that the odor pattern of the second odor data is identical to the previously stored odor pattern, and storing, by the controller, the odor pattern of the second odor data as a new odor pattern upon determining that the odor pattern of the second odor data is different from the previously stored odor pattern.

In another preferred embodiment, the method may further include controlling, by the controller, the inlet valve and the outlet valve to open in order to measure an odor of a new gas after acquiring the second odor data.

Another embodiment of the present invention provides a system for measuring odor data, the system including an odor measurement chamber including a gas inlet and a gas outlet formed in respective end portions thereof, an inlet valve mounted in the gas inlet so as to open and close, an outlet valve mounted in the gas outlet so as to open and close, a general-purpose odor sensor and at least three odor sensors disposed in the odor measurement chamber to sense an odor of a gas injected into the odor measurement chamber, and a controller configured to monitor first odor data of the gas for a sensing time period of the general-purpose odor sensor, to control the inlet valve and the outlet valve to close when variation in the monitored first odor data is equal to or greater than a reference value, and then to acquire second odor data of the gas sensed by one of the at least three odor sensors as actual odor data.

In a preferred embodiment, the at least three odor sensors may be configured to sense odors of mutually different kinds of specific gases.

In another preferred embodiment, the controller may be configured to compare an odor pattern of the second odor data with a previously stored odor pattern, to perform display control indicating that the odor pattern of the second odor data is identical to the previously stored odor pattern upon determining that the odor pattern of the second odor data is identical to the previously stored odor pattern, and to store the odor pattern of the second odor data as a new odor pattern upon determining that the odor pattern of the second odor data is different from the previously stored odor pattern.

In still another preferred embodiment, the controller may be configured to control the inlet valve and the outlet valve to open in order to measure an odor of a new gas after acquiring the second odor data.

A further embodiment of the present invention provides a method of measuring odor data, the method including injecting a gas, an odor of which is to be measured, into an odor measurement chamber, monitoring, by a controller, first odor data of the gas for a sensing time period of a general-purpose odor sensor disposed in the odor measurement chamber when the general-purpose odor sensor senses an odor of the gas, controlling, by the controller, an inlet valve and an outlet valve mounted in an inlet and an outlet of the odor measurement chamber, respectively, to close when variation in the monitored first odor data is equal to or greater than a reference value, and acquiring, by the controller, second odor data of the gas, sensed by one of at least three odor sensors disposed in the odor measurement chamber in a state of confining the gas in the odor measurement chamber by closing the inlet valve and the outlet valve, as actual odor data.

In a preferred embodiment, when one of the at least three odor sensors senses an odor of the gas, the at least three odor sensors may sense odors of mutually different kinds of specific gases.

In another preferred embodiment, the method may further include comparing, by the controller, an odor pattern of the second odor data with a previously stored odor pattern, performing, by the controller, display control indicating that the odor pattern of the second odor data is identical to the previously stored odor pattern upon determining that the odor pattern of the second odor data is identical to the previously stored odor pattern, and storing, by the controller, the odor pattern of the second odor data as a new odor pattern upon determining that the odor pattern of the second odor data is different from the previously stored odor pattern.

In still another preferred embodiment, the method may further include controlling, by the controller, the inlet valve and the outlet valve to open in order to measure an odor of a new gas after acquiring the second odor data.

Other aspects of preferred embodiments of the invention are discussed infra.

The above and other features of embodiments of the invention are discussed infra.

BRIEF DESCRIPTION OF THE DRAWINGS

The above and other features of embodiments of the present invention will now be described in detail with reference to certain exemplary embodiments thereof illustrated in the accompanying drawings which are given hereinbelow by way of illustration only, and thus are not limitative of embodiments of the present invention, and wherein.

6

Figure 1:
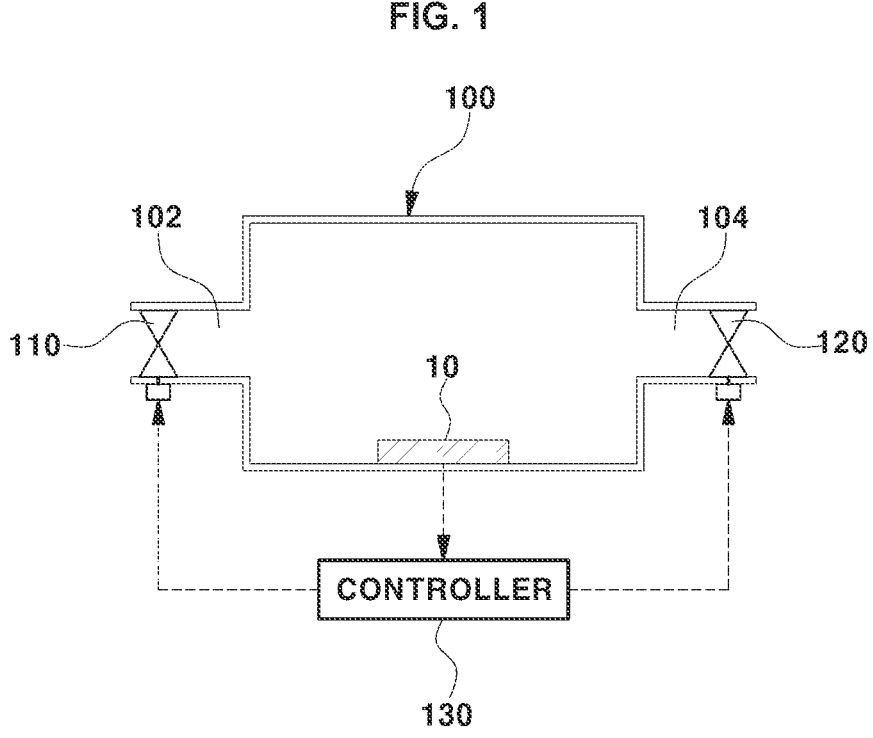
FIG. 1 is a configuration diagram showing a system for measuring odor data according to a first embodiment of the present invention.

It should be understood that the appended drawings are not necessarily to scale, presenting a somewhat simplified representation of various preferred features illustrative of the basic principles of embodiments of the invention. The specific design features of embodiments of the present invention as disclosed herein, including, for example, specific dimensions, orientations, locations, and shapes, will be determined in part by the particular intended application and use environment.

In the figures, reference numbers refer to the same or equivalent parts of embodiments of the present invention throughout the several figures of the drawings.

DETAILED DESCRIPTION OF ILLUSTRATIVE EMBODIMENTS

Various exemplary embodiments will now be described more fully with reference to the accompanying drawings, in which only some exemplary embodiments are shown. Specific structural and functional details disclosed herein are merely representative for the purpose of describing exemplary embodiments. Embodiments of the present invention, however, may be embodied in many alternate forms, and should not be construed as being limited only to the exemplary embodiments set forth herein. Accordingly, while exemplary embodiments of the invention are capable of being variously modified and taking alternative forms, embodiments thereof are shown by way of example in the drawings and will herein be described in detail. It should be understood, however, that there is no intent to limit the embodiments of the present invention to the particular exemplary embodiments disclosed. On the contrary, exemplary embodiments are to cover all modifications, equivalents, and alternatives falling within the scope of the invention.

It will be understood that, although the terms "first", "second", etc. may be used herein to describe various elements, these elements should not be limited by these terms. These terms are only used to distinguish one element from another. For example, a first element could be termed a second element, and, similarly, a second element could be termed a first element, without departing from the scope of the exemplary embodiments of the present invention.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between", "adjacent" versus "directly adjacent", etc.).

Wherever possible, the same reference numbers will be used throughout the drawings to refer to the same or like parts. The terminology used herein is for the purpose of describing particular embodiments only and is not intended to be limiting of exemplary embodiments of the invention. As used herein, the singular forms "a", "an", and "the" are intended to include the plural forms as well, unless the context clearly indicates otherwise. It will be further understood that the terms "comprises", "comprising", "includes", and/or "including", when used herein, specify the presence of stated components, steps, operations, and/or elements, but do not preclude the presence or addition of one or more other components, steps, operations, and/or elements.

Hereinafter, exemplary embodiments of the present invention will be described in detail with reference to the accompanying drawings.

First Embodiment

FIG. 1 is a configuration diagram showing a system for measuring odor data according to a first embodiment of the present invention. In FIG. 1, reference numeral 100 denotes an odor measurement chamber.

The odor measurement chamber 100 may be manufactured in a sealed box structure having a predetermined internal volume using a transparent plate, such as an acrylic plate.

The odor measurement chamber 100 includes a gas inlet 102 formed in one side portion thereof to introduce a gas, an odor of which is to be measured, into the odor measurement chamber 100 and a gas outlet 104 formed in the opposite side portion thereof to discharge the gas introduced into the odor measurement chamber 100 to the outside.

In addition, an inlet valve 110 and an outlet valve 120 are mounted in the gas inlet 102 and the gas outlet 104 of the odor measurement chamber 100, respectively, so as to open and close.

The inlet valve 110 and the outlet valve 120 may be electric valves that open or close in response to an electrical control signal of a controller.

In particular, one odor sensor 10 configured to sense an odor of the gas introduced into the odor measurement chamber 100 is disposed in the odor measurement chamber 100.

The odor sensor 10 senses an odor of the gas introduced into the odor measurement chamber 100 and transmits data on the sensed odor to the controller 130.

The controller 130 monitors first odor data of the gas for a time period for which the odor is primarily sensed by the odor sensor 10. When variation in the monitored first odor data is equal to or greater than a reference value, the controller 130 controls the inlet valve 110 and the outlet valve 120 to close and acquires second odor data of the gas secondarily sensed by the odor sensor 10 as actual odor data.

In detail, the controller 130 monitors the first odor data of the gas for the primary sensing time period of the odor sensor 10. When variation in the monitored first odor data is equal to or greater than the reference value, the controller 130 determines that odor components of the gas are in a state of being uniformly distributed in the odor measurement chamber 100 and controls the inlet valve 110 and the outlet valve 120 to close in order to temporarily confine the gas in the odor measurement chamber 100.

In the state in which the gas is temporarily confined in the odor measurement chamber 100, i.e., in the state in which the odor components of the gas are uniformly distributed in the odor measurement chamber 100, the odor sensor 10 secondarily senses the odor of the gas. In this way, a time point at which the odor sensor 10 accurately senses the odor of the gas may be determined. In addition, the controller 130 acquires the second odor data of the gas secondarily sensed by the odor sensor 10 as actual odor data. Accordingly, it is possible to stably and accurately obtain odor data at all times.

In addition, after acquiring the second odor data, the controller 130 controls the inlet valve 110 and the outlet valve 120 to open in order to measure an odor of a new gas.

In addition, the controller 130 compares the odor pattern of the second odor data with a previously stored odor pattern. When the two odor patterns are identical to each other, the controller 130 performs display control indicating that the odor pattern of the second odor data is identical to the previously stored odor pattern and stores the odor pattern of the second odor data. When the two odor patterns are different from each other, the controller 130 stores the odor pattern of the second odor data as a new odor pattern.

Hereinafter, a method of measuring odor data according to the first embodiment of the present invention will be described.

Figure 2:
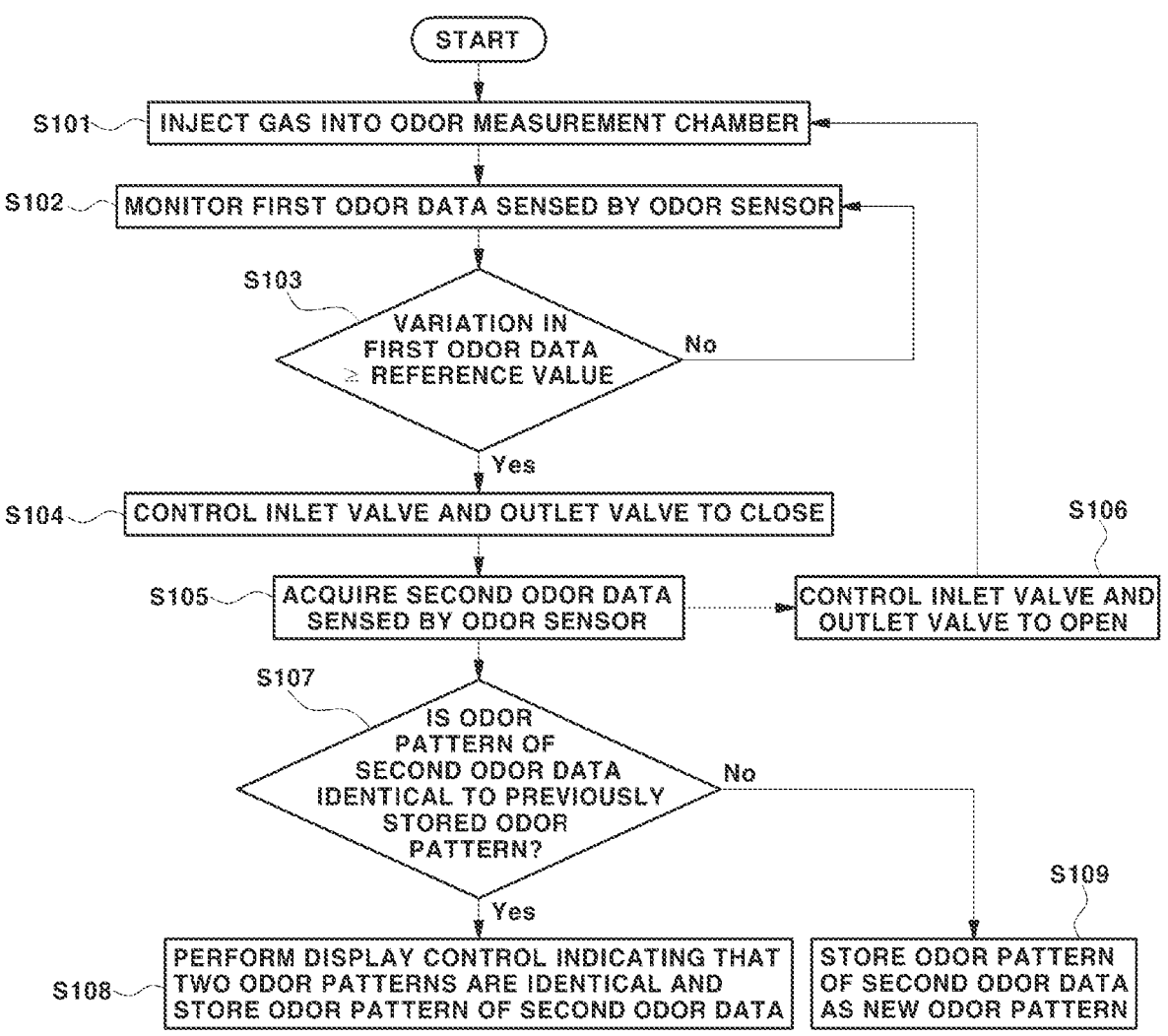
FIG. 2 is a flowchart showing a method of measuring odor data according to the first embodiment of the present invention.

FIG. 2 is a flowchart showing a method of measuring odor data according to the first embodiment of the present invention.

First, a gas, an odor of which is to be measured, is injected into the odor measurement chamber 100 (S101).

After the gas, the odor of which is to be measured, is injected into the odor measurement chamber 100 through the gas inlet 102, the odor sensor 10 disposed in the odor measurement chamber 100 may sense the odor of the gas and may transmit data on the sensed odor to the controller 130 when the gas flows to the gas outlet 104 via an inner space in the odor measurement chamber 100.

Subsequently, when the odor sensor 10 disposed in the odor measurement chamber 100 senses the odor of the gas, the controller 130 monitors first odor data of the gas in real time for a sensing time period of the odor sensor 10 (S102).

Subsequently, the controller 130 determines whether variation in the first odor data is equal to or greater than a reference value (S103).

Upon determining that variation in the first odor data is equal to or greater than the reference value, the controller 130 determines that the odor components of the gas are in a state of being uniformly distributed in the odor measurement chamber 100 to an extent enabling accurate sensing of the odor sensor 10 and controls the inlet valve 110 and the outlet valve 120 mounted in the gas inlet 102 and the gas outlet 104 of the odor measurement chamber 100, respectively, to close (S104).

As the inlet valve 110 and the outlet valve 120 are controlled to close, the gas may be temporarily confined in the odor measurement chamber 100, and the odor components of the gas may be maintained in the state of being uniformly distributed in the odor measurement chamber 100 to an extent enabling accurate sensing of the odor sensor 10.

Subsequently, when the odor sensor 10 senses the odor of the gas in the state in which the gas is temporarily confined in the odor measurement chamber 100, the controller 130 acquires second odor data of the gas as actual odor data for a sensing time period of the odor sensor 10 (S105).

In detail, in the state in which the gas is temporarily confined in the odor measurement chamber 100, i.e., in the state in which the odor components of the gas are uniformly distributed in the odor measurement chamber 100, the odor sensor 10 secondarily senses the odor of the gas. In this way, a time point at which the odor sensor 10 accurately senses the odor of the gas may be determined. In addition, the controller 130 acquires the second odor data of the gas secondarily sensed by the odor sensor 10 as actual odor data. Accordingly, it is possible to stably and accurately obtain odor data at all times.

In addition, after acquiring the second odor data, the controller 130 controls the inlet valve 110 and the outlet valve 120 to open in order to measure an odor of a new gas (S106).

In addition, after acquiring the second odor data, the controller 130 compares the odor pattern of the second odor data with a previously stored odor pattern (S107).

Upon determining that the odor pattern of the second odor data and the previously stored odor pattern are identical to each other, the controller 130 performs display control indicating that the odor pattern of the second odor data is identical to the previously stored odor pattern and stores the odor pattern of the second odor data (S108).

On the other hand, upon determining that the odor pattern of the second odor data and the previously stored odor pattern are different from each other, the controller 130 stores the odor pattern of the second odor data as a new odor pattern (S109).

After the odor pattern of the second odor data, which is identical to or different from the previously stored odor pattern, is stored in the controller 130, the same may be used to analyze causes of various kinds of odors generated in various industrial sites, vehicles, future mobility vehicles, or the like, and may also be used as analysis data for removal of the odors.

Second Embodiment

Figure 3:
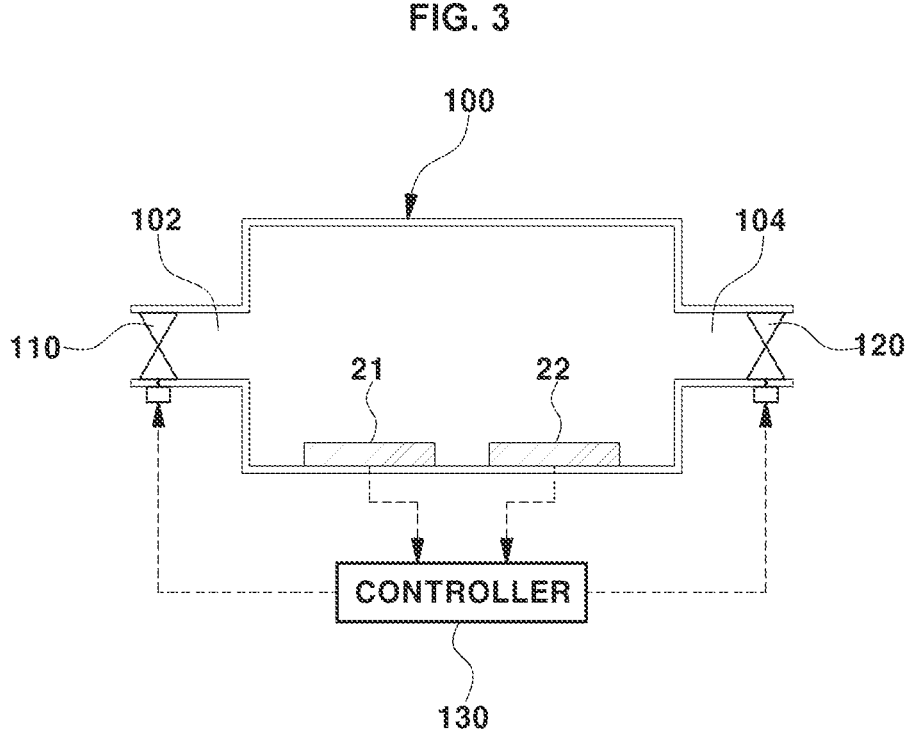
FIG. 3 is a configuration diagram showing a system for measuring odor data according to a second embodiment of the present invention.

FIG. 3 is a configuration diagram showing a system for measuring odor data according to a second embodiment of the present invention. In FIG. 3, reference numeral 100 denotes an odor measurement chamber.

The odor measurement chamber 100 may be manufactured in a sealed box structure having a predetermined internal volume using a transparent plate, such as an acrylic plate.

The odor measurement chamber 100 includes a gas inlet 102 formed in one side portion thereof to introduce a gas, an odor of which is to be measured, into the odor measurement chamber 100 and a gas outlet 104 formed in the opposite side portion thereof to discharge the gas introduced into the odor measurement chamber 100 to the outside.

In addition, an inlet valve 110 and an outlet valve 120 are mounted in the gas inlet 102 and the gas outlet 104 of the odor measurement chamber 100, respectively, so as to open and close.

The inlet valve 110 and the outlet valve 120 may be electric valves that open or close in response to an electrical control signal of a controller.

In particular, two odor sensors configured to sense an odor of the gas introduced into the odor measurement chamber 100 are disposed in the odor measurement chamber 100. The two odor sensors include a first odor sensor 21 and a second odor sensor 22.

The first odor sensor 21 and the second odor sensor 22 sense an odor of the gas introduced into the odor measurement chamber 100, and transmit data on the sensed odor to the controller 130.

The controller 130 monitors first odor data of the gas for a time period for which the odor is primarily sensed by the first odor sensor 21. When variation in the monitored first odor data is equal to or greater than a reference value, the controller 130 controls the inlet valve 110 and the outlet valve 120 to close and acquires second odor data of the gas secondarily sensed by the second odor sensor 22 as actual odor data.

In detail, the controller 130 monitors the first odor data of the gas for the primary sensing time period of the first odor sensor 21. When variation in the monitored first odor data is equal to or greater than the reference value, the controller 130 determines that odor components of the gas are in a state of being uniformly distributed in the odor measurement chamber 100 and controls the inlet valve 110 and the outlet valve 120 to close in order to temporarily confine the gas in the odor measurement chamber 100.

In the state in which the gas is temporarily confined in the odor measurement chamber 100, i.e., in the state in which the odor components of the gas are uniformly distributed in the odor measurement chamber 100, the second odor sensor 22 secondarily senses the odor of the gas. In this way, a time point at which the second odor sensor 22 accurately senses the odor of the gas may be determined. In addition, the controller 130 acquires the second odor data of the gas secondarily sensed by the second odor sensor 22 as actual odor data. Accordingly, it is possible to stably and accurately obtain odor data at all times.

In addition, after acquiring the second odor data sensed by the second odor sensor 22, the controller 130 controls the inlet valve 110 and the outlet valve 120 to open in order to measure an odor of a new gas.

In addition, the controller 130 compares the odor pattern of the second odor data sensed by the second odor sensor 22 with a previously stored odor pattern. When the two odor patterns are identical to each other, the controller 130 performs display control indicating that the odor pattern of the second odor data is identical to the previously stored odor pattern and stores the odor pattern of the second odor data. When the two odor patterns are different from each other, the controller 130 stores the odor pattern of the second odor data as a new odor pattern.

On the contrary, the controller 130 may monitor the odor data of the gas sensed by the second odor sensor 22 as the first odor data, may control the inlet valve 110 and the outlet valve 120 to close, and may acquire the second odor data of the gas sensed by the first odor sensor 21 as actual odor data.

In detail, the controller 130 may monitor the first odor data of the gas for the primary sensing time period of the second odor sensor 22. When variation in the monitored first odor data is equal to or greater than the reference value, the controller 130 may control the inlet valve 110 and the outlet valve 120 to close and may acquire the second odor data of the gas secondarily sensed by the first odor sensor 21 as actual odor data.

Hereinafter, a method of measuring odor data according to the second embodiment of the present invention will be described.

Figure 4:
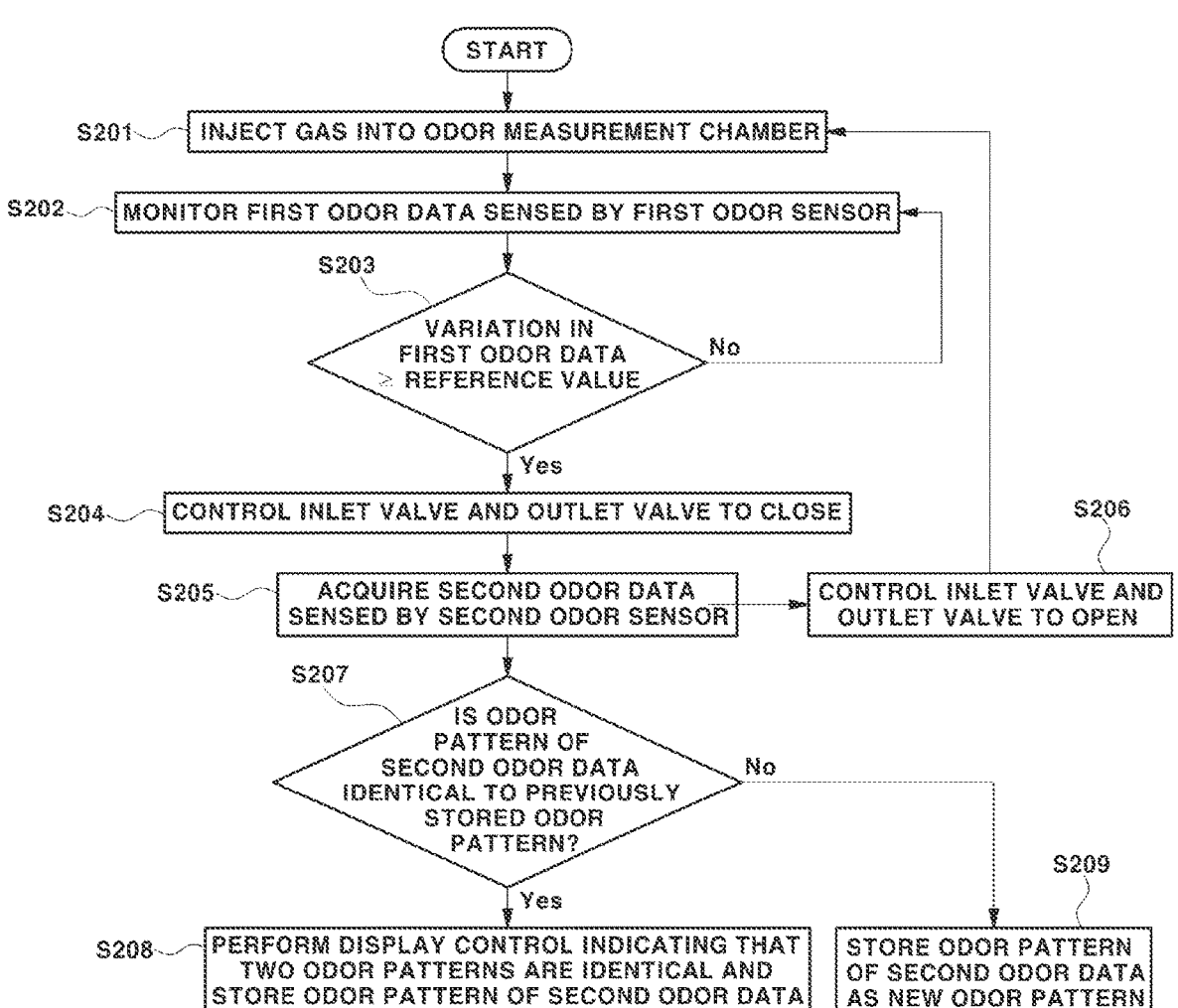
FIG. 4 is a flowchart showing a method of measuring odor data according to the second embodiment of the present invention.

FIG. 4 is a flowchart showing a method of measuring odor data according to the second embodiment of the present invention.

First, a gas, an odor of which is to be measured, is injected into the odor measurement chamber 100 (S201).

After the gas, the odor of which is to be measured, is injected into the odor measurement chamber 100 through the gas inlet 102, the first odor sensor 21 and the second odor sensor 22 disposed in the odor measurement chamber 100 may sense the odor of the gas and may transmit data on the sensed odor to the controller 130 when the gas flows to the gas outlet 104 via an inner space in the odor measurement chamber 100.

Subsequently, when the first odor sensor 21 disposed in the odor measurement chamber 100 senses the odor of the gas, the controller 130 monitors first odor data of the gas in real time for a sensing time period of the first odor sensor 21 (S202).

Subsequently, the controller 130 determines whether variation in the first odor data sensed by the first odor sensor 21 is equal to or greater than a reference value (S203).

Upon determining that variation in the first odor data is equal to or greater than the reference value, the controller 130 determines that the odor components of the gas are in a state of being uniformly distributed in the odor measurement chamber 100 to an extent enabling accurate sensing of the second odor sensor 22 and controls the inlet valve 110 and the outlet valve 120 mounted in the gas inlet 102 and the gas outlet 104 of the odor measurement chamber 100, respectively, to close (S204).

As the inlet valve 110 and the outlet valve 120 are controlled to close, the gas may be temporarily confined in the odor measurement chamber 100, and the odor components of the gas may be maintained in the state of being uniformly distributed in the odor measurement chamber 100 to an extent enabling accurate sensing of the second odor sensor 22.

Subsequently, when the second odor sensor 22 senses the odor of the gas in the state in which the gas is temporarily confined in the odor measurement chamber 100, the controller 130 acquires second odor data of the gas as actual odor data for a sensing time period of the second odor sensor 22 (S205).

In detail, in the state in which the gas is temporarily confined in the odor measurement chamber 100, i.e., in the state in which the odor components of the gas are uniformly distributed in the odor measurement chamber 100, the second odor sensor 22 secondarily senses the odor of the gas. In this way, a time point at which the second odor sensor 22 accurately senses the odor of the gas may be determined. In addition, the controller 130 acquires the second odor data of the gas secondarily sensed by the second odor sensor 22 as actual odor data. Accordingly, it is possible to stably and accurately obtain odor data at all times.

In addition, after acquiring the second odor data sensed by the second odor sensor 22, the controller 130 controls the inlet valve 110 and the outlet valve 120 to open in order to measure an odor of a new gas (S206).

In addition, after acquiring the second odor data, the controller 130 compares the odor pattern of the second odor data with a previously stored odor pattern (S207).

Upon determining that the odor pattern of the second odor data and the previously stored odor pattern are identical to each other, the controller 130 performs display control indicating that the odor pattern of the second odor data is identical to the previously stored odor pattern and stores the odor pattern of the second odor data (S208).

On the other hand, upon determining that the odor pattern of the second odor data and the previously stored odor pattern are different from each other, the controller 130 stores the odor pattern of the second odor data as a new odor pattern (S209).

After the odor pattern of the second odor data, which is identical to or different from the previously stored odor pattern, is stored in the controller 130, the same may be used to analyze causes of various kinds of odors generated in various industrial sites, vehicles, future mobility vehicles, or the like, and may also be used as analysis data for removal of the odors.

Meanwhile, the function of the first odor sensor 21 and the function of the second odor sensor 22 may be interchanged. That is, the second odor sensor 22 may be used to monitor variation in the odor data, and the first odor sensor 21 may be used to acquire actual odor data.

In detail, the controller 130 may monitor the first odor data of the gas for the primary sensing time period of the second odor sensor 22. When variation in the monitored first odor data is equal to or greater than the reference value, the controller 130 may control the inlet valve 110 and the outlet valve 120 to close and may acquire the second odor data of the gas secondarily sensed by the first odor sensor 21 as actual odor data.

Third Embodiment

Figure 5:
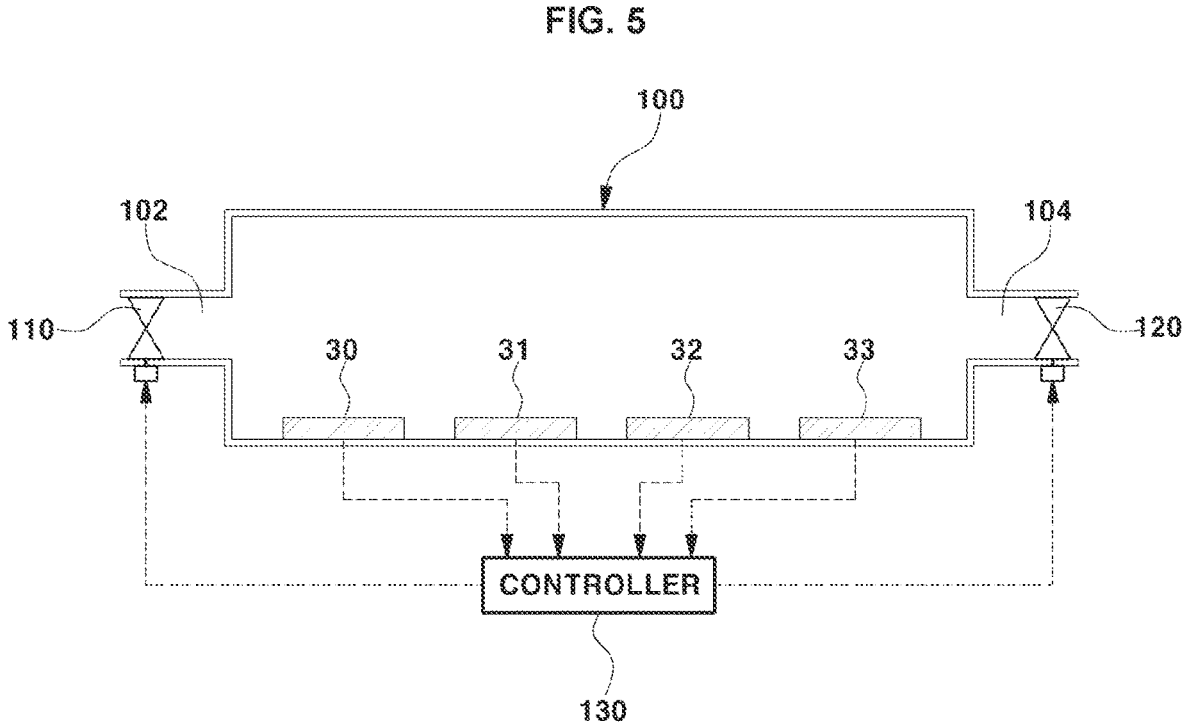
FIG. 5 is a configuration diagram showing a system for measuring odor data according to a third embodiment of the present invention.

FIG. 5 is a configuration diagram showing a system for measuring odor data according to a third embodiment of the present invention. In FIG. 5, reference numeral 100 denotes an odor measurement chamber.

The odor measurement chamber 100 may be manufactured in a sealed box structure having a predetermined internal volume using a transparent plate, such as an acrylic plate.

The odor measurement chamber 100 includes a gas inlet 102 formed in one side portion thereof to introduce a gas, an odor of which is to be measured, into the odor measurement chamber 100 and a gas outlet 104 formed in the opposite side portion thereof to discharge the gas introduced into the odor measurement chamber 100 to the outside.

In addition, an inlet valve 110 and an outlet valve 120 are mounted in the gas inlet 102 and the gas outlet 104 of the odor measurement chamber 100, respectively, so as to open and close.

The inlet valve 110 and the outlet valve 120 may be electric valves that open or close in response to an electrical control signal of a controller.

In particular, a general-purpose odor sensor 30 and at least three different types of odor sensors 31, 32, and 33 are disposed in the odor measurement chamber 100 in order to sense an odor of the gas introduced into the odor measurement chamber 100.

The general-purpose odor sensor 30 may be an odor sensor capable of sensing odors of various kinds of gases, without being limited to any specific gas, and the at least three different types of odor sensors 31, 32, and 33 may be odor sensors that sense odors of mutually different kinds of specific gases.

For example, the general-purpose odor sensor 30 may sense an odor of gas A, an odor of gas B, and an odor of gas C, without being limited to any specific gas, but has a shortcoming in that data on the sensed odor is not accurate. Among the at least three different types of odor sensors 31, 32, and 33, the first odor sensor 31 may precisely sense an odor of gas A, the second odor sensor 32 may precisely sense an odor of gas B, and the third odor sensor 33 may precisely sense an odor of gas C.

The general-purpose odor sensor 30 and the at least three different types of odor sensors 31, 32, and 33 sense an odor of the gas introduced into the odor measurement chamber 100 and transmit data on the sensed odor to the controller 130.

The controller 130 monitors first odor data of the gas for a time period for which the odor is primarily sensed by the general-purpose odor sensor 30. When variation in the monitored first odor data is equal to or greater than a reference value, the controller 130 controls the inlet valve 110 and the outlet valve 120 to close and acquires second odor data of the gas sensed by one of the at least three odor sensors 31, 32, and 33 as actual odor data.

In detail, the controller 130 monitors the first odor data of the gas for the primary sensing time period of the general-purpose odor sensor 30. When variation in the monitored first odor data is equal to or greater than the reference value, the controller 130 determines that odor components of the gas are in a state of being uniformly distributed in the odor measurement chamber 100 and controls the inlet valve 110 and the outlet valve 120 to close in order to temporarily confine the gas in the odor measurement chamber 100.

In the state in which the gas is temporarily confined in the odor measurement chamber 100, i.e., in the state in which the odor components of the gas are uniformly distributed in the odor measurement chamber 100, one of the at least three odor sensors 31, 32, and 33 secondarily senses the odor of the gas. In this way, a time point at which one of the at least three odor sensors 31, 32, and 33 accurately senses the odor of the gas may be determined. In addition, the controller 130 acquires the second odor data of the gas secondarily sensed by one of the at least three odor sensors 31, 32, and 33 as actual odor data. Accordingly, it is possible to stably and accurately obtain odor data at all times.

In addition, after acquiring the second odor data sensed by one of the at least three odor sensors 31, 32, and 33, the controller 130 controls the inlet valve 110 and the outlet valve 120 to open in order to measure an odor of a new gas.

In addition, the controller 130 compares the odor pattern of the second odor data sensed by one of the at least three odor sensors 31, 32, and 33 with a previously stored odor pattern. When the two odor patterns are identical to each other, the controller 130 performs display control indicating that the odor pattern of the second odor data is identical to the previously stored odor pattern and stores the odor pattern of the second odor data. When the two odor patterns are different from each other, the controller 130 stores the odor pattern of the second odor data as a new odor pattern.

Hereinafter, a method of measuring odor data according to the third embodiment of the present invention will be described.

Figure 6:
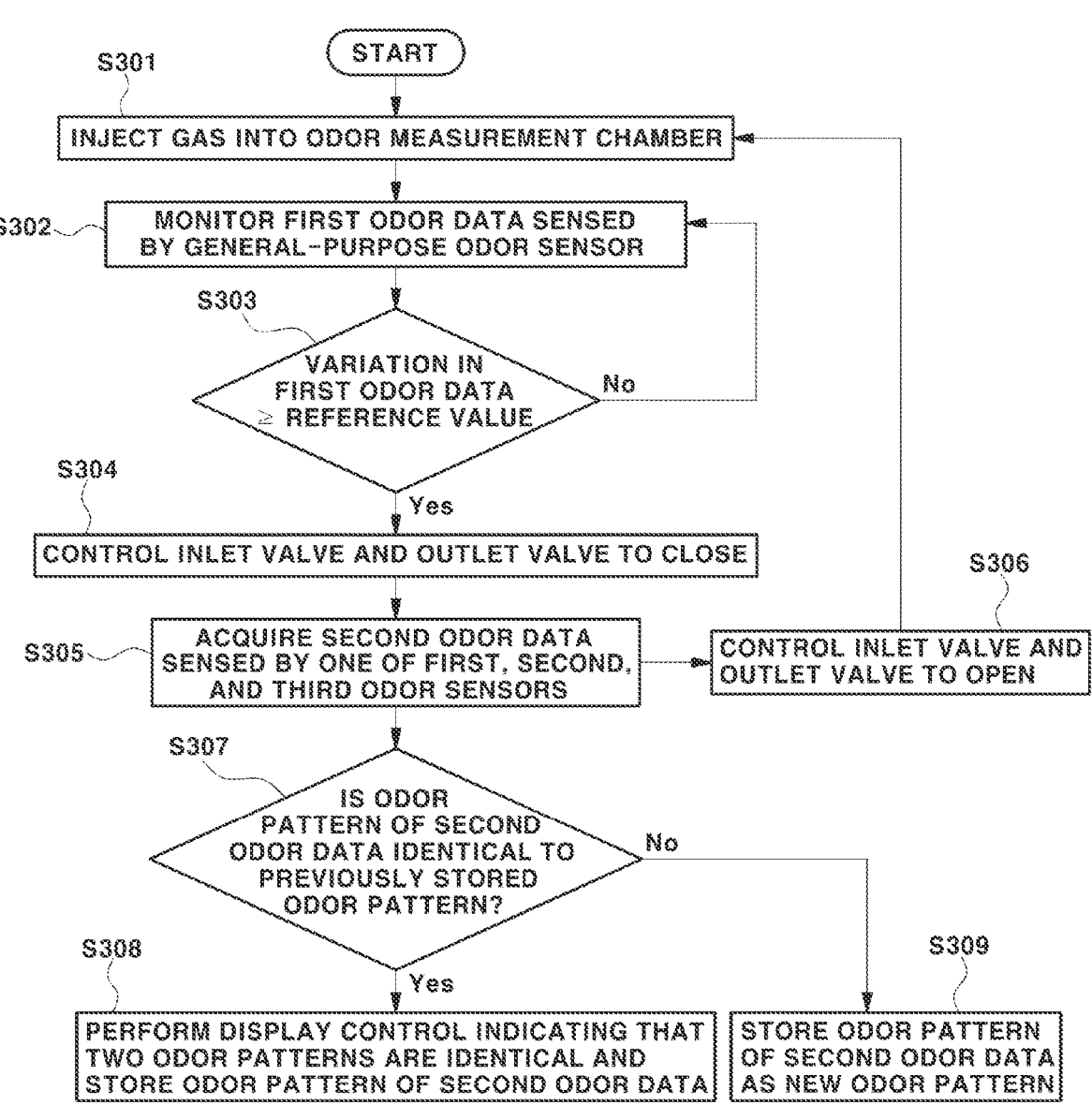
FIG. 6 is a flowchart showing a method of measuring odor data according to the third embodiment of the present invention.

FIG. 6 is a flowchart showing a method of measuring odor data according to the third embodiment of the present invention.

First, a gas, an odor of which is to be measured, is injected into the odor measurement chamber 100 (S301).

After the gas, the odor of which is to be measured, is injected into the odor measurement chamber 100 through the gas inlet 102, the general-purpose odor sensor 30 and the different types of odor sensors 31, 32, and 33 disposed in the odor measurement chamber 100 may sense the odor of the gas and may transmit data on the sensed odor to the controller 130 when the gas flows to the gas outlet 104 via an inner space in the odor measurement chamber 100.

In this case, when the gas injected into the odor measurement chamber 100 is one of gas A, gas B, and gas C, the general-purpose odor sensor 30 may sense an odor of the injected gas among gas A, gas B, and gas C. Among the different types of odor sensors 31, 32, and 33, the first odor sensor 31 may sense an odor of gas A, the second odor sensor 32 may sense an odor of gas B, and the third odor sensor 33 may sense an odor of gas C.

Subsequently, when the general-purpose odor sensor 30 disposed in the odor measurement chamber 100 senses the odor of the gas, the controller 130 monitors first odor data of the gas in real time for a sensing time period of the general-purpose odor sensor 30 (S302).

Subsequently, the controller 130 determines whether variation in the first odor data sensed by the general-purpose odor sensor 30 is equal to or greater than a reference value (S303).

Upon determining that variation in the first odor data sensed by the general-purpose odor sensor 30 is equal to or greater than the reference value, the controller 130 determines that the odor components of the gas are in a state of being uniformly distributed in the odor measurement chamber 100 to an extent enabling accurate sensing of one of the different types of odor sensors 31, 32, and 33 and controls the inlet valve 110 and the outlet valve 120 mounted in the gas inlet 102 and the gas outlet 104 of the odor measurement chamber 100, respectively, to close (S304).

As the inlet valve 110 and the outlet valve 120 are controlled to close, the gas may be temporarily confined in the odor measurement chamber 100, and the odor components of the gas may be maintained in the state of being uniformly distributed in the odor measurement chamber 100 to an extent enabling accurate sensing of one of the different types of odor sensors 31, 32, and 33.

Subsequently, when one of the different types of odor sensors 31, 32, and 33 senses the odor of the gas in the state in which the gas is temporarily confined in the odor measurement chamber 100, the controller 130 acquires second odor data of the gas as actual odor data for a sensing time period of one of the different types of odor sensors 31, 32, and 33 (S305).

For example, in the state in which gas A is temporarily confined in the odor measurement chamber 100, when the first odor sensor 31 among the different types of odor sensors 31, 32, and 33 senses the odor of gas A, the controller 130 acquires second odor data of gas A as actual odor data for a sensing time period of the first odor sensor 31.

Alternatively, in the state in which gas B is temporarily confined in the odor measurement chamber 100, when the second odor sensor 32 among the different types of odor sensors 31, 32, and 33 senses the odor of gas B, the controller 130 acquires second odor data of gas B as actual odor data for a sensing time period of the second odor sensor 32.

Alternatively, in the state in which gas C is temporarily confined in the odor measurement chamber 100, when the third odor sensor 33 among the different types of odor sensors 31, 32, and 33 senses the odor of gas C, the controller 130 acquires second odor data of gas C as actual odor data for a sensing time period of the third odor sensor 33.

In detail, in the state in which the gas is temporarily confined in the odor measurement chamber 100, i.e., in the state in which the odor components of the gas are uniformly distributed in the odor measurement chamber 100, one of the different types of odor sensors 31, 32, and 33 secondarily senses the odor of the gas. In this way, a time point at which one of the different types of odor sensors 31, 32, and 33 accurately senses the odor of the gas may be determined. In addition, the controller 130 acquires the second odor data of the gas secondarily sensed by one of the different types of odor sensors 31, 32, and 33 as actual odor data. Accordingly, it is possible to stably and accurately obtain odor data at all times.

In addition, after acquiring the second odor data sensed by one of the different types of odor sensors 31, 32, and 33, the controller 130 controls the inlet valve 110 and the outlet valve 120 to open in order to measure an odor of a new gas (S306).

In addition, after acquiring the second odor data, the controller 130 compares the odor pattern of the second odor data with a previously stored odor pattern (S307).

Upon determining that the odor pattern of the second odor data and the previously stored odor pattern are identical to each other, the controller 130 performs display control indicating that the odor pattern of the second odor data is identical to the previously stored odor pattern and stores the odor pattern of the second odor data (S308).

On the other hand, upon determining that the odor pattern of the second odor data and the previously stored odor pattern are different from each other, the controller 130 stores the odor pattern of the second odor data as a new odor pattern (S309).

After the odor pattern of the second odor data, which is identical to or different from the previously stored odor pattern, is stored in the controller 130, the same may be used to analyze causes of various kinds of odors generated in various industrial sites, vehicles, future mobility vehicles, or the like and may also be used as analysis data for removal of the odors.

As is apparent from the above description, embodiments of the present invention have the following effects.

First, a gas, an odor of which is to be measured, is injected into an odor measurement chamber, and variation in odor data of the gas is monitored. When variation in the monitored odor data is equal to or greater than a reference value, an inlet valve and an outlet valve mounted in the odor measurement chamber are controlled to close in order to confine the gas in the odor measurement chamber. In this state, odor data of the gas sensed by an odor sensor is acquired as actual odor data. Accordingly, it is possible to stably and accurately obtain odor data at all times.

In other words, when variation in the monitored odor data is equal to or greater than the reference value, it is determined that odor components of the gas are in a state of being uniformly distributed in the odor measurement chamber, and odor data of the gas sensed by the odor sensor in the state in which the gas is confined in the odor measurement chamber is acquired as actual odor data. Accordingly, it is possible to stably and accurately obtain odor data at all times.

Second, the odor data measurement system according to embodiments of the present invention may be mounted not only in various types of vehicles but also in future mobility vehicles, such as purpose built vehicles (PBVs) or urban air mobility (UAM) vehicles, in order to measure various kinds of odors generated therein. Accordingly, it is possible to clearly analyze actual causes of odors based on the measured odor data and to improve the emotional quality related to odors of various types of vehicles and future mobility vehicles.

Third, the odor data measurement system according to embodiments of the present invention may be mounted in robots designed to easily access various industrial sites, whereby the scope of function of the robots may be extended to a function of accurately measuring components of odors generated in various industrial sites and concentrations of the odor components.

Embodiments of the present invention have been described above with reference to exemplary embodiments. The embodiments described in the specification and shown in the accompanying drawings are illustrative only and are not intended to represent all embodiments of the invention. Therefore, the embodiments of the present invention are not limited to the embodiments presented herein, and it is to be understood by those skilled in the art that various modifications or changes can be made without departing from the technical spirit or scope of the invention as disclosed in the appended claims.

What is claimed is:

1. A system for measuring odor data, the system comprising:

an odor measurement chamber comprising a gas inlet and a gas outlet located at respective end portions of the odor measurement chamber;

an inlet valve mounted in the gas inlet;

an outlet valve mounted in the gas outlet;

an odor sensor disposed in the odor measurement chamber; and a controller configured to monitor first odor data of gas injected into the odor measurement chamber for a sensing time period of the odor sensor, to control the inlet valve and the outlet valve to close in response to a variation in the monitored first odor data being equal to or greater than a reference value, and then to acquire second odor data of the gas sensed by the odor sensor as actual odor data.

2. The system of claim 1, wherein the controller is configured to:

compare an odor pattern of the second odor data with a previously stored odor pattern;

in response to a determination that the odor pattern of the second odor data is identical to the previously stored odor pattern, perform display control indicating that the odor pattern of the second odor data is identical to the previously stored odor pattern; and in response to a determination that the odor pattern of the second odor data is different from the previously stored odor pattern, store the odor pattern of the second odor data as a new odor pattern.

3. The system of claim 1, wherein the controller is configured to control the inlet valve and the outlet valve to open in order to measure an odor of a new gas after acquiring the second odor data.

4. A method of measuring odor data, the method comprising:

injecting a gas into an odor measurement chamber;

monitoring first odor data of the gas for a sensing time period of an odor sensor disposed in the odor measurement chamber when the odor sensor senses an odor of the gas;

controlling an inlet valve and an outlet valve mounted in an inlet and an outlet of the odor measurement chamber, respectively, to close in response to a variation in the monitored first odor data being equal to or greater than a reference value; and acquiring second odor data of the gas, sensed by the odor sensor in a state of confining the gas in the odor measurement chamber by closing the inlet valve and the outlet valve, as actual odor data.

5. The method of claim 4, further comprising:

comparing an odor pattern of the second odor data with a previously stored odor pattern;

in response to a determination that the odor pattern of the second odor data is identical to the previously stored odor pattern, performing display control indicating that the odor pattern of the second odor data is identical to the previously stored odor pattern; and in response to a determination that the odor pattern of the second odor data is different from the previously stored odor pattern, storing the odor pattern of the second odor data as a new odor pattern.

6. The method of claim 4, further comprising controlling the inlet valve and the outlet valve to open in order to measure an odor of a new gas after acquiring the second odor data.

7. A system for measuring odor data, the system comprising:

an odor measurement chamber comprising a gas inlet and a gas outlet located at respective end portions of the odor measurement chamber;

an inlet valve mounted in the gas inlet;

an outlet valve mounted in the gas outlet;

a first odor sensor and a second odor sensor disposed in the odor measurement chamber; and a controller configured to monitor first odor data of a gas injected into the odor measurement chamber for a sensing time period of the first odor sensor, to control the inlet valve and the outlet valve to close in response to a variation in the monitored first odor data being equal to or greater than a reference value, and then to acquire second odor data of the gas sensed by the second odor sensor as actual odor data.

8. The system of claim 7, wherein the controller is configured to:

compare an odor pattern of the second odor data with a previously stored odor pattern;

in response to a determination that the odor pattern of the second odor data is identical to the previously stored odor pattern, perform display control indicating that the odor pattern of the second odor data is identical to the previously stored odor pattern; and in response to a determination that the odor pattern of the second odor data is different from the previously stored odor pattern, store the odor pattern of the second odor data as a new odor pattern.

9. The system of claim 7, wherein the controller is configured to control the inlet valve and the outlet valve to open in order to measure an odor of a new gas after the second odor data is acquired.

10. A method of measuring odor data, the method comprising:

injecting a gas into an odor measurement chamber;

monitoring first odor data of the gas for a sensing time period of a first odor sensor disposed in the odor measurement chamber in response to the first odor sensor sensing the odor of the gas;

controlling an inlet valve and an outlet valve mounted in an inlet and an outlet of the odor measurement chamber, respectively, to close in response to a variation in the monitored first odor data being equal to or greater than a reference value; and acquiring second odor data of the gas as actual odor data, the second odor data acquired by sensing by a second odor sensor disposed in the odor measurement chamber in a state of confining the gas in the odor measurement chamber by closing the inlet valve and the outlet valve.

11. The method of claim 10, further comprising:

comparing an odor pattern of the second odor data with a previously stored odor pattern;

in response to a determination that the odor pattern of the second odor data is identical to the previously stored odor pattern, performing display control indicating that the odor pattern of the second odor data is identical to the previously stored odor pattern; and in response to a determination that the odor pattern of the second odor data is different from the previously stored odor pattern, storing the odor pattern of the second odor data as a new odor pattern.

12. The method of claim 10, further comprising controlling the inlet valve and the outlet valve to open in order to measure an odor of a new gas after acquiring the second odor data.

13. A system for measuring odor data, the system comprising:

an odor measurement chamber comprising a gas inlet and a gas outlet located at respective end portions of the odor measurement chamber;

an inlet valve mounted in the gas inlet;

an outlet valve mounted in the gas outlet;

a general-purpose odor sensor and at least three particular odor sensors disposed in the odor measurement chamber; and a controller configured to monitor first odor data of a gas injected into the odor measurement chamber for a sensing time period of the general-purpose odor sensor, to control the inlet valve and the outlet valve to close in response to a variation in the monitored first odor data being equal to or greater than a reference value, and to acquire, as actual odor data, second odor data of the gas sensed by one particular odor sensor of the at least three particular odor sensors.

14. The system of claim 13, wherein the at least three particular odor sensors are configured to sense odors of mutually different kinds of specific gases.

15. The system of claim 13, wherein the controller is configured to:

compare an odor pattern of the second odor data with a previously stored odor pattern;

in response to a determination that the odor pattern of the second odor data is identical to the previously stored odor pattern, perform display control indicating that the odor pattern of the second odor data is identical to the previously stored odor pattern; and in response to a determination that the odor pattern of the second odor data is different from the previously stored odor pattern, store the odor pattern of the second odor data as a new odor pattern.

16. The system of claim 13, wherein the controller is configured to control the inlet valve and the outlet valve to open in order to measure an odor of a new gas after acquiring the second odor data.

17. A method of measuring odor data, the method comprising:

injecting a gas into an odor measurement chamber;

monitoring first odor data of the gas for a sensing time period of a general-purpose odor sensor disposed in the odor measurement chamber when the general-purpose odor sensor senses an odor of the gas;

controlling an inlet valve and an outlet valve mounted in an inlet and an outlet of the odor measurement chamber, respectively, to close in response to a variation in the monitored first odor data being equal to or greater than a reference value; and acquiring second odor data of the gas as actual odor data, the second odor data being acquired by sensing by one particular odor sensor of at least three particular odor sensors disposed in the odor measurement chamber in a state of confining the gas in the odor measurement chamber by closing the inlet valve and the outlet valve.

18. The method of claim 17, wherein the at least three particular odor sensors sense odors of mutually different kinds of specific gases.

19. The method of claim 17, further comprising:

comparing an odor pattern of the second odor data with a previously stored odor pattern;

in response to a determination that the odor pattern of the second odor data is identical to the previously stored odor pattern, performing display control indicating that the odor pattern of the second odor data is identical to the previously stored odor pattern; and in response to a determination that the odor pattern of the second odor data is different from the previously stored odor pattern, storing the odor pattern of the second odor data as a new odor pattern.

20. The method of claim 17, further comprising controlling, the inlet valve and the outlet valve to open in order to measure an odor of a new gas after acquiring the second odor data.

* * * * *